United States Patent
Ernsperger et al.

(10) Patent No.: US 9,232,983 B2
(45) Date of Patent: Jan. 12, 2016

(54) METHOD AND APPARATUS FOR DETERMINING THE ILLUMINATION BEAM DOSE IN SURGICAL FIELD ILLUMINATION

(75) Inventors: Stefan Ernsperger, Ellwangen (DE); Peter Reimer, Ellwangen (DE)

(73) Assignee: Carl Zeiss Meditec AG, Jena (DE)

( * ) Notice: Subject to any disclaimer, the term of this patent is extended or adjusted under 35 U.S.C. 154(b) by 761 days.

(21) Appl. No.: 12/865,920

(22) PCT Filed: Feb. 4, 2009

(86) PCT No.: PCT/EP2009/000998
§ 371 (c)(1),
(2), (4) Date: Dec. 6, 2010

(87) PCT Pub. No.: WO2009/098092
PCT Pub. Date: Aug. 13, 2009

(65) Prior Publication Data
US 2011/0066408 A1 Mar. 17, 2011

(30) Foreign Application Priority Data
Feb. 8, 2008 (DE) .......................... 10 2008 008 475

(51) Int. Cl.
*G06F 7/60* (2006.01)
*G06F 17/10* (2006.01)
(Continued)

(52) U.S. Cl.
CPC ........ *A61B 19/5202* (2013.01); *G06F 17/5009* (2013.01); *A61B 3/13* (2013.01); *A61B 19/5223* (2013.01); *A61B 2019/505* (2013.01); *F21V 23/0442* (2013.01); *F21W 2131/205* (2013.01);
(Continued)

(58) Field of Classification Search
CPC . G06F 17/5009; G06F 19/3437; G06F 19/12; G06F 19/321; G02B 21/361; G02B 21/0012; G02B 21/0076; A61B 19/5223; A61B 2019/505
USPC ..................................... 703/2, 5, 7
See application file for complete search history.

(56) References Cited

U.S. PATENT DOCUMENTS 4,657,013 A  4/1987  Hoerenz et al.
5,962,857 A * 10/1999  McKeever et al. ......... 250/484.5
(Continued)

FOREIGN PATENT DOCUMENTS

DE  10 2005 055 058   5/2007
DE     102005055058   5/2007
(Continued)

*Primary Examiner* — Omar Fernandez Rivas
*Assistant Examiner* — Angel Calle
(74) *Attorney, Agent, or Firm* — Nixon Peabody LLP; Jeffrey L. Costellia

(57) ABSTRACT

A method is disclosed for determining an illumination beam dose in surgical field illumination. Said method comprises the following steps: at least one actual illumination-relevant value is sensed; and an illumination beam dose is calculated from said sensed actual value. Sensing of the actual illumination-relevant value includes sensing of a value of at least one adjustable parameter of an illumination device. Furthermore, simulated dose characteristics associated with the adjustable parameter are selected, at least one simulated dose value is calculated taking into account the value of the adjustable parameter and the associated simulated dose characteristics, and the illumination beam dose is calculated taking into account the at least one simulated dose value. Also disclosed are an apparatus, a computer program product, and a surgical microscope for carrying out said method.

24 Claims, 3 Drawing Sheets

(51) Int. Cl.
   *G06G 7/48* (2006.01)
   *G06G 7/56* (2006.01)
   *A61B 19/00* (2006.01)
   *G06F 17/50* (2006.01)
   *G02B 21/00* (2006.01)
   *G06F 19/00* (2011.01)
   *G06F 19/12* (2011.01)
   *G02B 21/36* (2006.01)
   *A61B 3/13* (2006.01)
   *F21V 23/04* (2006.01)
   *F21W 131/205* (2006.01)

(52) U.S. Cl.
   CPC ......... *G02B 21/0012* (2013.01); *G02B 21/0076* (2013.01); *G02B 21/361* (2013.01); *G06F 19/12* (2013.01); *G06F 19/321* (2013.01); *G06F 19/3437* (2013.01)

(56) References Cited

U.S. PATENT DOCUMENTS

| | | | |
|---|---|---|---|
| 6,151,383 | A | 11/2000 | Xue et al. |
| 6,233,310 | B1 * | 5/2001 | Relihan et al. ................. 378/108 |
| 6,607,527 | B1 * | 8/2003 | Ruiz et al. ........................ 606/41 |
| 6,987,834 | B2 * | 1/2006 | Omernick et al. ............. 378/109 |
| 7,505,201 | B2 | 3/2009 | Oelckers et al. |
| 7,933,066 | B2 | 4/2011 | Steffen et al. |
| 2002/0118449 | A1 | 8/2002 | Spink |
| 2004/0165696 | A1 * | 8/2004 | Lee .................................. 378/65 |
| 2005/0203492 | A1 * | 9/2005 | Nguyen et al. ..................... 606/4 |
| 2007/0167748 | A1 | 7/2007 | Rietzel |
| 2008/0002811 | A1 * | 1/2008 | Allison ............................ 378/65 |

FOREIGN PATENT DOCUMENTS

| | | | |
|---|---|---|---|
| DE | 10 2008 008 475 | 8/2009 | |
| EP | 1 069 807 | 1/2001 | |
| EP | 1069807 A2 * | 1/2001 | ............... H05G 1/46 |

* cited by examiner

METHOD AND APPARATUS FOR DETERMINING THE ILLUMINATION BEAM DOSE IN SURGICAL FIELD ILLUMINATION

BACKGROUND OF THE INVENTION

1. Field of the Invention

The invention relates to a method for determining the illumination beam dose in surgical field illumination, comprising the steps of registering at least one illumination-relevant state value and calculating an illumination beam dose on the basis of the registered state value, and the invention also relates to an apparatus, an operating microscope and a computer program product therefor.

2. Description of the Related Art

In the case of surgery in which radiation-sensitive tissue has to be subjected to a certain illumination beam dose in order to be able to carry out the surgery, for example in the case of opthalmosurgical operations (eye operations), the prior art has disclosed the use of dosimeters. Such dosimeters measure the dose from an electromagnetic or particle radiation, for example the light used to illuminate the surgical region, and can be integrated into the surgical field illumination of an operating microscope.

The German laid-open specification DE 36 10 024 A1 discloses an illumination strength dose device for operating microscopes. In this, the radiation or light dose is measured by first of all sampling a small fraction of the field illumination flux generated by the microscope-internal illumination apparatus. Sampling is undertaken by arranging a transparent plane plate with sufficient scattering in the illumination beam path, with a photodetector being arranged on the edge of said plate. The electrical signal from the photodetector in respect of the radiation measured thus is then registered in a microprocessor and integrated over time.

However, this procedure does not take into account the fact that light of different wavelengths has a different effect on the radiation-sensitive tissue. It is therefore disadvantageous in that, for example, radiation of less damaging light wavelengths is evaluated the same as radiation of more damaging light wavelengths and therefore a maximum remaining surgery time estimated on the basis of the dose result is lower than what is actually possible.

This is particularly problematic if the spectral components of the light generated by the light sources vary according to desired brightness, or if the light source is interchanged during surgery or if spectral filters are used.

In order to solve these problems, the German laid-open specification DE 10 2005 055 058 A1 discloses a system that carries out a spectrally-weighted measurement of the generated light. For this, the light is measured by a plurality of sensors, for example one sensor for each of infrared, visible and ultraviolet light, and said light is registered by a microprocessor. Herein, the spectral weighting overall is attained by the respective spectral sensitivity of the sensors. The microprocessor registers the measured values weighted spectrally in this fashion, compares these to the corresponding biological radiation hazard limits and calculates the resulting remaining surgery duration therefrom.

However, the measurement elements required for this are relatively complex and expensive, and supply only limited or practically no usable results if external additional or special light sources are utilized.

Hence, it is an object of the present invention to specify a method for determining the illumination beam dose in surgical field illumination, which operates reliably, reduces the required technical complexity but nevertheless allows the effects of different light spectra and illumination situations to be taken into account.

SUMMARY OF THE INVENTION

The invention relates to a method for determining an illumination beam dose in surgical field illumination, for example from an operating microscope and more particularly from an opthalmological operating microscope. The method includes the steps of registering at least one illumination-relevant state value and calculating an illumination beam dose on the basis of the registered state value. The step of registering the illumination-relevant state value includes registering a setting parameter value of at least one setting parameter of an illumination apparatus, selecting a dose simulation characteristic assigned to the setting parameter, and calculating at least one dose simulation value is calculated taking into account the setting parameter value and the assigned dose simulation characteristic. The illumination beam dose is calculated taking into account the at least one dose simulation value.

Registering the setting parameter values of the illumination apparatus and using these as the basis of a calculation for a simulated illumination radiation dose brings about a technically simple solution that operates reliably. The complexity in terms of required measurement sensors and the measurement noise generated by the surgical surroundings are reduced in comparison with conventional solutions because in this case registered radiation measured values do not, or do not exclusively, form the basis of the calculation. The setting parameter values to be registered are generally available in any case in the control for the illumination apparatus and can therefore be recalled without much complexity.

The dose simulation characteristic used for the simulation calculations and assigned to the setting parameter can accordingly be selected such that it reproduces the contribution to the illumination beam dose of a component of the illumination apparatus influenced by the setting parameter.

Instead of, or in addition to, the measurement of the emerging brightness, the radiation and spectral property of all illumination apparatuses or illumination means is determined in this fashion by calculation and simulation as a function of the control by the user thereof, i.e. the corresponding control signals.

By way of example, the invention can be developed by virtue of the fact that selecting the dose simulation characteristic includes selecting a calculation function. At the same time, or alternatively, selecting the dose simulation characteristic can include selecting a tabular storage allocation with setting parameter values and function values.

The tabular storage allocation can be imported into the method by means of a data storage medium from a product supplier or in other ways of data transmission. Embodiments of the method can generate the tabular storage allocation by the measurement of brightness values at selected setting parameter values.

The invention can furthermore be developed by virtue of the fact that registering the illumination-relevant state value furthermore includes registering a brightness measurement value. Here, an illumination beam dose can be calculated within the scope of determining a dose value from the registered brightness measurement value and modifying the dose value using the dose simulation value. As a result of this, the simulation result can be coupled to a registered measurement result, which however was obtained using technically simple measurement technology.

In embodiments of the invention, the brightness measurement value can be registered within the scope of registering a video image of at least part of the surgical region. The brightness measurement value can then be derived by calculation from the video image. This renders superfluous further complex measurement apparatuses, such as a sensor array staged according to spectral components or broadband radiation sensors.

Optionally, it is also possible for at least one dose simulation characteristic to be updated from time to time on the basis of the dose value determined on the basis of a registered brightness measurement value.

If the invention is developed to the extent that registering the illumination-relevant state value furthermore includes registering a surgery characteristic value and the dose simulation value is calculated as a function of the surgery characteristic value, typical surgical situations can thus be incorporated in the calculation of the radiation dose, for example the presence of a clouded lens in the case of eye surgery, or a partial cover of the surgical region, which both act in a reducing fashion on the actually acting amount of radiation. Here, the surgery characteristic value can be derived by calculation from the video image, for example by suitable automatic image recognition means and statistical classification functions.

Variants of the invention can furthermore be designed such that registering the illumination-relevant state value furthermore includes registering a configuration state value and the dose simulation value is calculated as a function of the configuration state value. As a result of this, it is possible, for example, to include different types of illumination means, which can alternatively or simultaneously be inserted in illumination apparatuses, in accordance with their respective brightness-dependent spectral properties in the simulation calculation, or it is possible to take into account additional external filter or illumination apparatuses in accordance with their illumination-relevant contribution.

The invention also relates to an apparatus for determining an illumination beam dose in surgical field illumination according to the method described above. The apparatus includes a processor, a storage medium coupled to the processor, and an input/output interface coupled to the processor. The input/output interface is designed to register a setting parameter value of at least one setting parameter of a connectable illumination apparatus, the storage medium contains a dose simulation characteristic assigned to the setting parameter, the processor is designed to calculate at least one dose simulation value taking into account the setting parameter value and the assigned dose simulation characteristic, and the processor is furthermore designed to calculate the illumination beam dose taking into account the at least one dose simulation value.

This specifies an apparatus for carrying out the method illustrated above, which correspondingly implements the aforementioned advantageous effects.

Developments of the apparatus can be characterized in that the dose simulation characteristic assigned to the setting parameter reproduces the contribution to the illumination beam dose of a component of the illumination apparatus influenced by the setting parameter.

The input/output interface can be furthermore designed for registering a brightness measurement value and the processor can be designed to generate and/or adjust a dose simulation characteristic within the scope of assigning registered brightness measurement values to setting parameter values.

In embodiments, the processor can be designed to determine a dose value for calculating the illumination beam dose from the registered brightness measurement value and to modify the dose value using the dose simulation value.

If the input/output interface is designed for registering a video image and the processor is designed for calculating a brightness measurement value from the video image, a brightness measurement value is included in the calculation in a technically simple fashion. Furthermore, the processor can have an image recognition component that is designed to classify a registered video image within the scope of assigning a surgery characteristic value.

The input/output interface can additionally be designed to register a configuration state value and the processor is designed to calculate the dose simulation value furthermore as a function of the configuration state value.

The invention as claimed in claim 23 provides a computer program product stored on a computer-readable storage medium, which computer program product contains computer-readable program means for executing by means of a computer the steps of the method according to the invention.

The computer program product can correspondingly be stored on a magnetic or optical data storage medium, such as a CD-ROM, DVD-ROM, disk or hard-disk drive, or in a semiconductor component, such as a memory component or a memory part of a processor.

The invention also relates to an operating microscope, more particularly an opthalmological operating microscope, with an apparatus for determining an illumination beam dose in surgical field illumination. The apparatus can in this case be integrated into the computerized control system of the operating microscope, for example by installing and executing suitable program components in the control system.

Hereinbelow, the invention will be explained in an exemplary fashion on the basis of a plurality of figures.

DETAILED DESCRIPTION OF THE PREFERRED EMBODIMENTS

Figure 1:
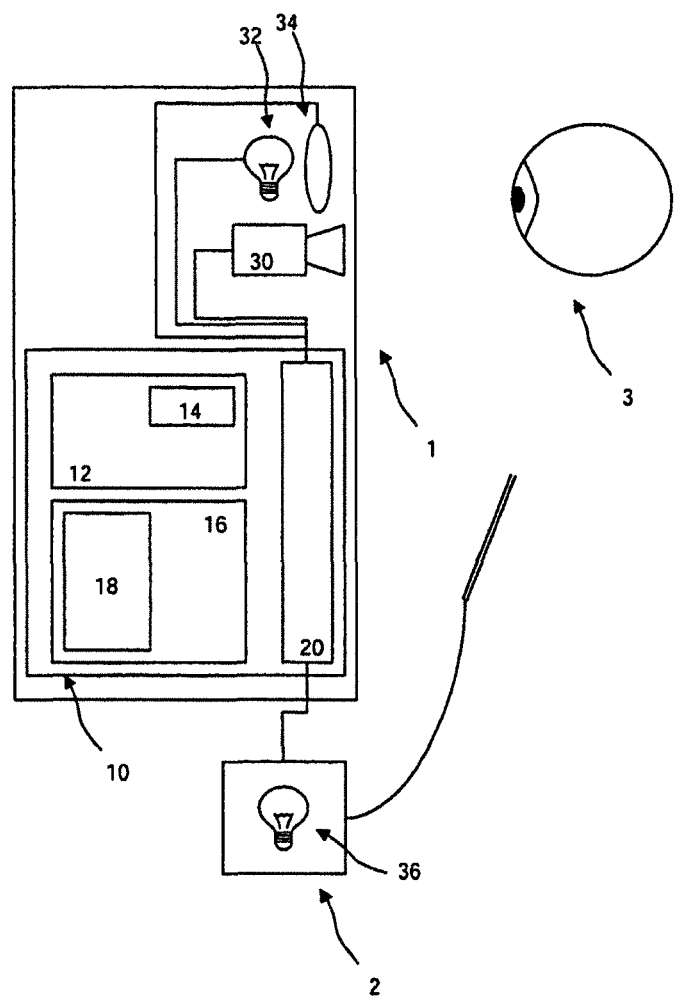
FIG. 1 shows a schematic overview over an exemplary embodiment of the apparatus for determining an illumination beam dose.

FIG. 1 shows a schematic overview over an exemplary embodiment of the apparatus for determining an illumination beam dose, which apparatus is integrated in a video operating microscope. The very schematically illustrated operating microscope contains an internal illumination apparatus 32, which during surgery emits a light dose onto the surgical region of the eye 3 through filters 34 that can be pivoted in by the user. A video camera 30 registers a temporal sequence of video images from the surgical region. Additionally, a second, external illumination apparatus 2 with illumination means 36 is used by the operator in order to illuminate the surgical field manually. The actual optical system of the microscope has not been illustrated for reasons of clarity. Although the apparatus according to the invention for determining an illumination beam dose is used in an operating microscope in the exemplary embodiment, it goes without saying that it can also be used in a purely optical operating microscope.

The operating microscope 1 contains an apparatus for determining an illumination beam dose 10, which apparatus in this case is implemented in the computerized control unit of the operating microscope, and has a processor 12, a storage medium 16 with a dose simulation characteristic 18 contained therein, and an input/output interface 20. The internal illumination apparatus 32 (illustrated here identically with the internal illumination means), stops 34 and/or filters that can be pivoted in, a video camera 30 and an external illumination apparatus 2 are connected to the dose determination apparatus 10 via the interface 20.

The operator can set a number of different parameters on the components or on the control unit, which controls the components, for operating the microscope 1, the illumination apparatus 32 and the filter apparatus 34. The respective setting parameter thus obtains a certain value. Setting parameters can relate to the brightness of a light source, or whether a filter 34, or a stop, has been pivoted in. The dose simulation characteristic 18 assigns dose simulation values to values of setting parameters, or combinations of such values, such that the light dose resulting from the setting and generated by the illumination apparatuses is determined as precisely as possible (possibly taking into account further parameters such as characteristic surgery situations or filters and stops). In the process, a plurality of dose simulation characteristics for various illumination apparatuses can be combined by calculation.

Thus, the dose simulation characteristic 18 can take into account e.g. the change in the spectrum of the light source in accordance with the set intensity, for example in the case of a halogen light source. For this, it is possible to select a function that approximates the family of characteristic curves for the light source. In the present example, corresponding families of characteristic curves are stored in tabular form in a discrete allocation table. It is also possible for non-continuous, clocked light sources to be modeled in dose simulation characteristics.

The dose simulation characteristic 18 can also take into account the effect of pivoted-in stops, such as slit illumination or a retina protection stop, or pivoted-in filters, such as gray or yellow filters. It is also possible to take account of manually entered parameters, such as parameters relating to the composition of the surgical object. Furthermore, it is possible for the dose simulation characteristics to take account of setting parameters affecting the illumination geometry, such as the illumination angle, spot diameter or the proportion of the surrounding illumination in the red reflex illumination.

A simple light sensor can be coupled to the dose determination apparatus instead of, or in addition to, the video camera 30, or the brightness value can be determined from the video image by calculation.

Embodiments of the dose determination apparatus 10 can contain an image recognition module 14, which can be realized by image recognition functions in the processor by software. The image recognition with subsequent classification can be designed such that it can be trained by learning processes of the artificial intelligence, such as neural networks, with and/or without feedback from the operator.

This can automatically determine surgery characteristics, i.e. category values of characteristic surgery situations, that can be taken into account in the dose simulation characteristics. Here, surgery characteristic values comprise the factor relating to whether the retina of the eye 3 is illuminated, whether parts of the retina are covered, for example by surgical instruments during the intervention, or whether the eye has a clouded lens.

Figure 2:
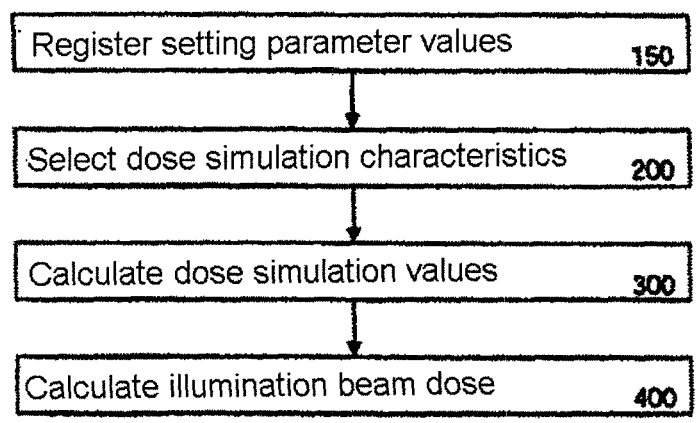
FIG. 2 shows a schematic overview over a first exemplary embodiment of the method for determining an illumination beam dose.
Figure 3:
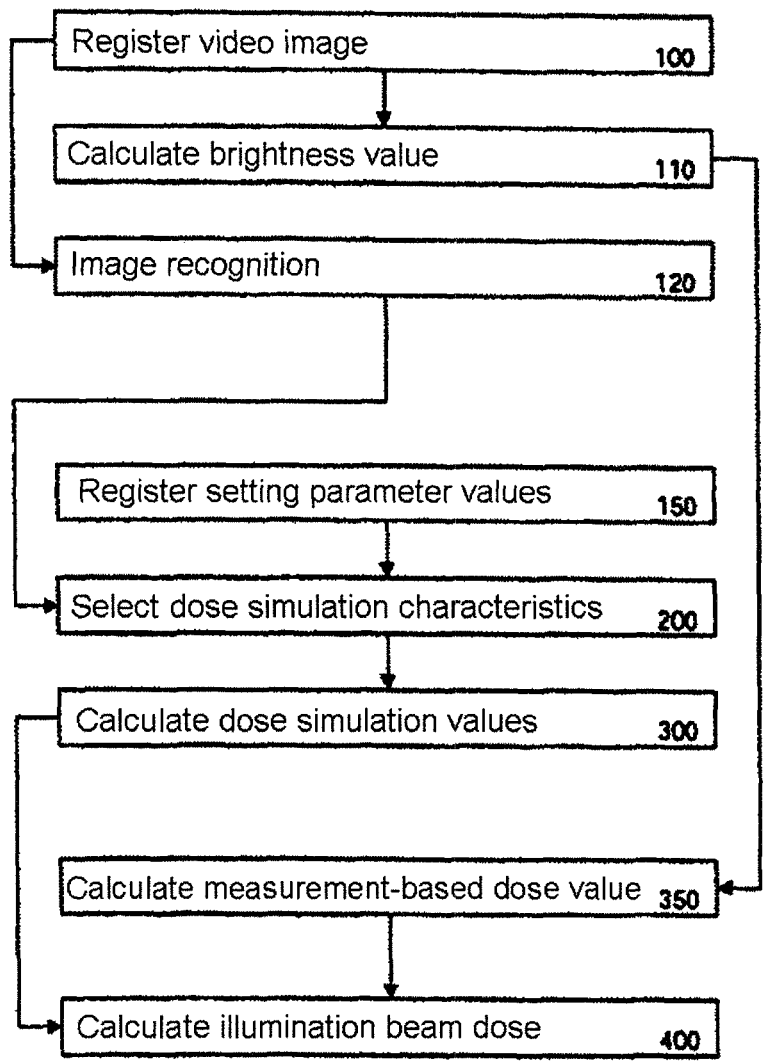
FIG. 3 shows an illustration of a second exemplary embodiment of the method for determining an illumination beam dose.

FIGS. 2 and 3 are used to explain the method of operation of the invention in more detail on the basis of the method realized therein by hardware and/or software.

FIG. 2 shows an embodiment of the method that comprises the basic elements of the simulation-based dose calculation. The current values of the setting parameters affecting the actually generated light dose are registered in step 150. Then, one or more dose simulation characteristics corresponding to the setting parameters are addressed in the storage medium in step 200 and the assigned dose simulation values are calculated in step 300. For this, if need be different individual values are determined and are then combined by calculation such that finally the simulated illumination beam dose is calculated in step 400.

This method can be extended such that the simulation values are combined with actually measured brightness values by calculation, and, furthermore, additional illumination-relevant framework conditions are taken into account, as shown in the exemplary embodiment as per FIG. 3.

FIG. 3 shows how one from a temporal succession of video images is registered successively or in parallel in step 100, and how setting parameter values for illumination, filter and stop apparatuses are registered in step 150. A brightness value is determined from the registered video image in step 110, on the basis of which brightness value a (measurement-based) dose value is calculated in step 350.

Additionally, a surgery characteristic value is determined, as described above, by means of image recognition functions from the video image registered in step 100, which surgery characteristic value is incorporated in the selection of the dose simulation characteristic in step 200 and/or in the corresponding calculation of the dose simulation values in step 300. Not illustrated in any more detail here is the registration of a configuration state value, which depends on the number and type of accessories, such as additional external light sources, connected to the apparatus. This registration step can also be carried out in parallel and be incorporated in the selection in step 200 and/or the calculation in step 300.

Finally, the dose simulation values are combined with the measurement-based dose values by calculation, and so the illumination beam dose is correspondingly calculated in step 400.

The proposed system thus provides a method and an apparatus for determining an illumination beam dose in surgical field illumination, which uses setting parameter values instead of, or in addition to, brightness measurement values to calculate the illumination beam dose and thus significantly reduces the measurement complexity of precise results. Furthermore, the system provides means for automatically undertaking a correction of the simulated calculation for various surgical situations and thus improves the quality of the prognosis overall.

Using the illumination beam dose calculated according to the invention, the processor can optionally determine the remaining surgery duration available, that is to say that amount of time that the eye (or a different surgical field) can still be illuminated by the current setting parameter values without being damaged. Furthermore, there is also the additional option of the processor—for example following a request by the surgeon—simulating remaining surgery durations on the basis of alternative setting parameters and providing, on the basis of the simulation, suggestions for alternative settings of the illumination apparatus that increase the remaining surgery duration.

The invention claimed is:

1. A method for determining a simulation-based illumination beam dose of light that will be emitted onto a surgical region by a light emitting illumination apparatus during a course of a surgery, comprising the following steps:

registering setting parameter values including characteristics of the illumination apparatus and at least one of: a presence or absence of a filter apparatus, a presence or absence of a stop, ambient light conditions and characteristics of a surgical site;

selecting, from a storage, dose simulation characteristics assigned to each of the registered setting parameters;

calculating dose simulation values (300) taking into account the registered setting parameters and the assigned dose simulation characteristics selected from the storage for each of the registered setting parameters; and calculating the simulation-based illumination beam dose taking into account the calculated dose simulation values, wherein the simulation-based illumination beam dose of light is emitted onto an eye by the light emitting illumination apparatus.

2. The method of claim 1, wherein the dose simulation characteristic assigned to the setting parameter reproduces a contribution to the illumination beam dose of a component of an illumination apparatus influenced by the setting parameter.

3. The method of claim 1, wherein selecting the dose simulation characteristic includes selecting a calculation function.

4. The method of claim 1, wherein selecting the dose simulation characteristic includes selecting a tabular storage allocation with setting parameter values and function values.

5. The method of claim 4, wherein the tabular storage allocation is generated by a measurement of brightness values at selected setting parameter values.

6. The method of claim 1, wherein registering the characteristics of the illumination apparatus includes registering (100, 110) a brightness measurement value.

7. The method of claim 6, wherein the step of calculating the illumination beam dose comprises:

determining (350) a dose value from the registered brightness measurement value, and modifying (400) the dose value using the dose simulation value.

8. The method of claim 6, wherein the step of registering the brightness measurement value comprises registering (100) a video image of at least part of a surgical region.

9. The method of claim 8, wherein the brightness measurement value is derived by calculation from the video image (110).

10. The method of claim 6, further comprising updating at least one dose simulation characteristic from time to time based on a dose value determined on a basis of the brightness measurement value that has been registered.

11. The method of claim 8, wherein registering the characteristics of a surgical site includes registering a surgery characteristic value and calculating the dose simulation value is carried out as a function of the surgery characteristic value.

12. The method of claim 11, wherein in that the surgery characteristic value is derived by calculation from the video image (120).

13. The method of claim 1, wherein the setting parameter values further includes a configuration state value and the dose simulation value is calculated as a function of the configuration state value.

14. The method of claim 1, wherein a remaining surgery duration is calculated based on the dose simulation value.

15. An apparatus for determining a simulation-based illumination beam dose of light emitted onto a surgical region, comprising:

a processor (12), a storage medium (16) coupled to the processor, and an input/output interface (20) coupled to the processor, wherein the input/output interface is designed to register setting parameter values including characteristics of the illumination apparatus and at least one of: a presence or absence of a filter pivoted into the light, a presence or absence of a stop pivoted into the light, ambient light conditions and characteristics of a surgical site;

the storage medium contains a dose simulation characteristic (18) assigned to each of the setting parameters, the processor is designed to calculate dose simulation values taking into account the registered setting parameters values and the assigned dose simulation characteristics, and the processor further is designed to calculate the simulation-based illumination beam dose taking into account the at least one dose simulation values, wherein the simulation-based illumination beam dose of light is emitted onto an eye by the light emitting illumination apparatus.

16. The apparatus of claim 15, wherein the dose simulation characteristics assigned to each of the setting parameters reproduces a contribution to the illumination beam dose of a component of the illumination apparatus influenced by the setting parameters.

17. The apparatus of claim 15, wherein the input/output interface further is designed for registering a brightness measurement value.

18. The apparatus of claim 17, wherein the processor is designed to generate and/or adjust the dose simulation characteristic while assigning registered brightness measurement values to setting parameter values.

19. The apparatus of claim 17, wherein the processor is designed to determine a dose value for calculating the illumination beam dose from the registered brightness measurement value and to modify the dose value using the dose simulation value.

20. The apparatus of claim 15, wherein the input/output interface is designed for registering a video image and for calculating a brightness measurement value from the video image.

21. The apparatus of claim 20, wherein the processor has an image recognition component (14) that is designed to classify the registered video image as part of assigning a surgery characteristic value.

22. The apparatus of claim 15, wherein the input/output interface is designed to register a configuration state value and the processor is designed to calculate the dose simulation value furthermore as a function of the configuration state value.

23. A computer program product stored on a non-transitory computer-readable storage medium, which computer program product contains computer-readable program means for executing by means of a computer the steps of the method of claim 1.

24. An operating microscope (1) with an apparatus for determining an illumination beam dose in surgical field illumination as claimed in claim 15.

* * * * *